June 1, 1965 C. L. KINNEY Plant Pat. 2,527
PEAR TREE
Filed Dec. 13, 1963
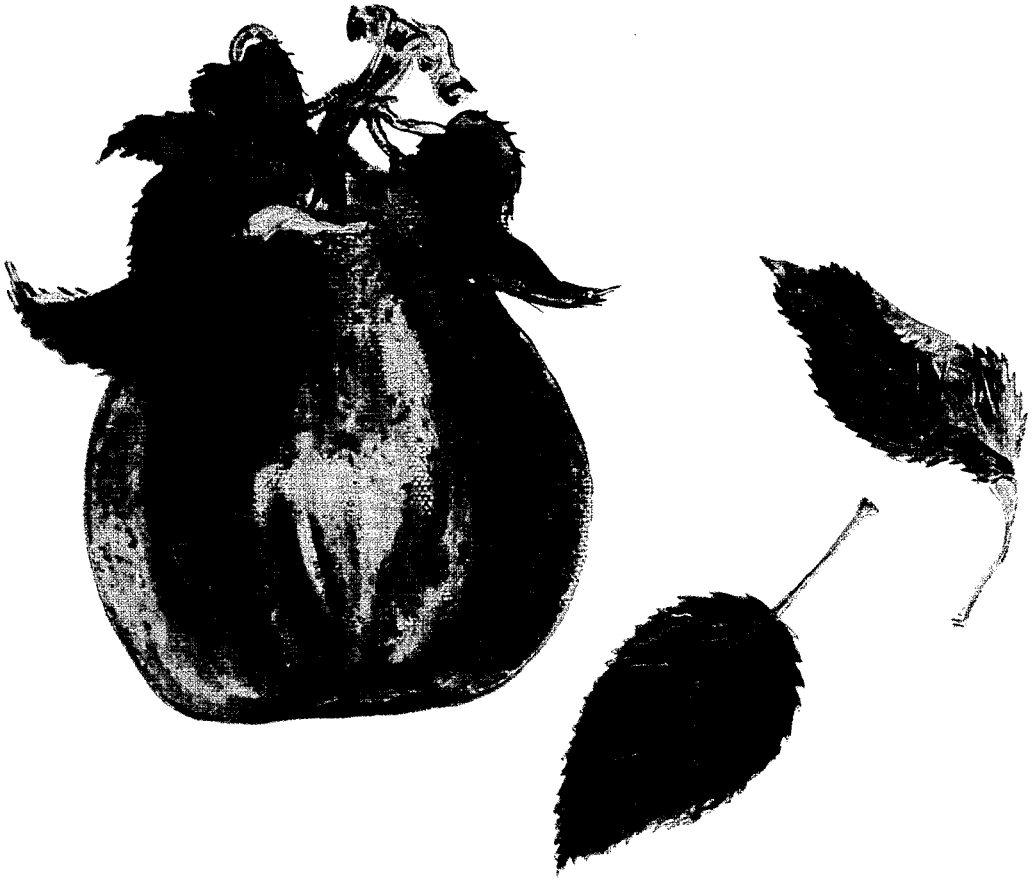

United States Patent Office

Plant Pat. 2,527
Patented June 1, 1965

2,527
PEAR TREE

Charles Lyle Kinney, 211 N. Berkeley Way,
Medford, Oreg.

Filed Dec. 13, 1963, Ser. No. 330,214
1 Claim. (Cl. Plt.—36)

The present invention relates to a new and distinct variety of pear tree originated as a sport of the variety known as Doyenné Du Comice, commonly referred to Comice (unpatented).

The present discovery originated as a sport thrown from a Comice pear tree in a cultivated orchard on my property in Jackson County, State of Oregon, adjacent Phoenix, Oregon. This property lies in the Bear Creek valley. Bear Creek is a tributary of Rogue River. The new variety was discovered by me in 1960.

The parent variety Comice is characterized by thick trunks and structural limbs, very upright growth, smooth bark except on older trees, of a grayish white color and a variety that enjoys vigorous growth. The blossom is white.

The new variety is substantially identical to Comice except that the bark is a reddish brown, and the blossom petals pink before folding outwardly, which petals fade to lighter shares of pink as they come into flower, opening and maturing as a pinkish white. The ripening time corresponds with that of Comice.

The fruit is strikingly different. Comice fruit is greenish yellow, becoming a fine yellow at maturity.

The new variety is a striking red varying in shading somewhat depending upon the degree of exposure to the sun.

Asexual reproduction of the new variety by grafting and budding was done by me on my property that is adjacent the property above defined, and establishes that the foregoing characteristic run true to form, are fixed, and are transmitted through succeeding propagations.

The accompanying photographic drawings are made from an oil painting and truly show a specimen of the fruit, its stem with several leaves thereon and two detached leaves to illustrate that the new variety responds substantially to its parent Comice, save as to the coloration of the fruit, although the leaves on the new variety are reddish when first unfolding, the red fading out to green with a red overcast as the leaves mature, as is illustrated in the accompanying drawings.

The following is a detailed description of the new variety, based upon observations of specimens grown in and around Phoenix, Oregon and in the Bear Creek valley, with color terminology in accordance with Dictionary of Color by Maerz and Paul (1950 Ed.), published by McGraw-Hill Book Co., except whenever the general color terms of ordinary dictionary significance are obvious:

Tree: Substantially identical to parent Comice.
- *Branches.*—Very upright, as in Comice.
- *Leaves.*—Distinctive with a tapering point, finely serrated and the color range between Plate 22: H–7 (Garland green) and Plate 24: H–9 (unnamed).

Fruit: Similar in size, shape, conformation and character to that of Comice.
- *Color.*—Coloration is an overall red having a slight purplish tint when the fruit is ripe, and has a mottled greenish-yellow undercoat, when it approaches ripeness. The overall red coloration ranges between Plate 7: H–6 (Burmese Ruby) to Plate 6: L–11 (Egyptian R Alcazar).
- *Flesh.*—White, fine, melting when ripe, eating quality the "very best."
- *Use.*—Market and dessert.
- *Keeping quality.*—Good.

I claim:

A new and distinct variety of pear tree substantially as shown and described, characterized as to novelty by its similarity to its parent variety Doyenné Du Comice, but distinguished therefrom by bearing fruit having an overall reddish skin having a slight purplish tint when the fruit is ripe and having said overall reddish skin with a mottled greenish-yellow undercoat, immediately prior to its attaining a stage of ripeness.

No references cited.

ABRAHAM G. STONE, *Primary Examiner.*